United States Patent

Tack

(10) Patent No.: US 8,617,101 B2
(45) Date of Patent: Dec. 31, 2013

(54) FLEXIBLE DRIVE FOR BREAST PUMP

(75) Inventor: Johannes Willem Tack, Zuidhorn (NL)

(73) Assignee: Koninklijke Philips N.V., Eindhoven (NL)

( * ) Notice: Subject to any disclaimer, the term of this patent is extended or adjusted under 35 U.S.C. 154(b) by 7 days.

(21) Appl. No.: 13/384,389

(22) PCT Filed: Jul. 21, 2010

(86) PCT No.: PCT/IB2010/053319
§ 371 (c)(1),
(2), (4) Date: Jan. 17, 2012

(87) PCT Pub. No.: WO2011/013037
PCT Pub. Date: Feb. 3, 2011

(65) Prior Publication Data
US 2012/0116299 A1 May 10, 2012

(30) Foreign Application Priority Data

Jul. 28, 2009 (EP) .................................. 09166532

(51) Int. Cl.
*A61M 1/06* (2006.01)
(52) U.S. Cl.
USPC .............................................. 604/74; 604/315
(58) Field of Classification Search
USPC .............................. 604/74, 315; 417/474, 515
See application file for complete search history.

(56) References Cited

U.S. PATENT DOCUMENTS

| 6,808,517 B2 * | 10/2004 | Greter et al. ................... 604/500 |
| 2001/0038799 A1 | 11/2001 | Silver et al. |
| 2004/0039330 A1 * | 2/2004 | Silver ............................. 604/74 |
| 2008/0275386 A1 | 11/2008 | Myers |

FOREIGN PATENT DOCUMENTS

| WO | 03082378 A1 | 10/2003 |
| WO | 2005016409 A2 | 2/2005 |

* cited by examiner

*Primary Examiner* — Laura Bouchelle

(57) ABSTRACT

A drive mechanism for generating a negative pressure in a vacuum chamber (32/132) of a breast pump (10/110), the drive mechanism comprising a housing (12/112), a motor (14/114) coupled to a rotatable drive element within the housing, a resilient membrane (28/128) coupled to the housing and, a flexible strap (50/150) coupled between the drive element and the resilient membrane. Rotation of the drive element causes the flexible strap to pull and resiliently deform the resilient membrane to create the negative pressure in a vacuum chamber of a breast pump. Also, a breast pump including such a drive mechanism together with a vacuum chamber (32/132) coupled to the housing (12/112). The vacuum chamber comprises a receptacle and a breast-receiving funnel (40/140) in fluid communication with the receptacle, wherein when a woman's breast is placed in the breast-receiving funnel, the vacuum chamber is sealed closed such that deformation the resilient membrane (28/128) creates a negative pressure in the vacuum chamber.

13 Claims, 2 Drawing Sheets

FLEXIBLE DRIVE FOR BREAST PUMP

FIELD OF THE INVENTION

The invention relates to breast pumps, and more specifically to drive mechanisms for vacuum creation in breast pumps and breast pumps incorporating such drive mechanisms.

BACKGROUND OF THE INVENTION

A breast pump is a device used by mothers for expressing their breast milk into a baby feeding bottle. Such devices can be either manually operated or automated by incorporation of, for example, an electric motor to drive the device. Such devices often include a flexible membrane which is moved up and down to create a negative pressure in a vacuum chamber of the breast pump, and include a rack and pinion mechanism in which the pinion rotates back and forth to move the rack, which is connected to the membrane, linearly back and forth to generate the negative pressure. Alternatively, a crank shaft or cam/eccentric element may be employed to move the membrane back and forth to generate the negative pressure.

It is known that the hormone 'prolactin' which promotes the milk ejection reflex is only effectively produced when the mother is in a relaxed condition. However, it can be unpleasant and/or uncomfortable for a mother to use a breast pump as it can feel unnatural since the device may feel and sound overly 'mechanical'. Therefore, the discomfort and/or unnatural feel of using the breast pump may not put the mother at ease and may make her feel anxious, thereby affecting her capability to express milk for her baby.

Furthermore, the above-mentioned known mechanisms for negative pressure creation in known breast pumps include sliding surfaces and/or frictional contact which produce wear and/or may require lubrication to minimize wear. These mechanisms may create mechanical noise themselves and can also effectively transmit vibrations of the motor and gearbox to the outside structure of the breast pump such as the housing and/or milk collection bottle.

Reference WO 2005/016409 discloses a breast pump utilizing a rack and pinion type mechanism to generate linear movement for operation of the breast pump piston and cylinder. US2001/0038799 discloses a breast pump that has a durable drive chain comprising a drive shaft fit with an eccentric cam, to which is attached a follower. The follower being pivotably connected to a puller that is attached to a flexible diaphragm for creating a negative pressure in the breast pump.

SUMMARY OF THE INVENTION

It would be advantageous to provide a drive mechanism for a breast pump, and a breast pump incorporating such a drive mechanism, which substantially alleviates or overcomes the problems mentioned above. To address this concern, in a first aspect of the present invention, a drive mechanism for a breast pump is provided comprising a housing, a motor coupled to a rotatable drive element within the housing, a resilient membrane coupled to the housing, and a flexible strap coupled between the drive element and the membrane, wherein rotation of the drive element causes the flexible strap to pull and resiliently deform the resilient membrane to create the negative pressure in a vacuum chamber of a breast pump. The drive element may comprise a drive wheel and the flexible strap may be coupled to the drive wheel such that rotation of the drive wheel causes the flexible strap to be wound around the drive wheel.

The drive wheel may include a plurality of teeth and the flexible strap may include a corresponding shaped plurality of teeth formed on one side thereof for engagement with the teeth on the drive wheel.

The resilient membrane may include a bellows section which is deformed when the flexible strap pulls on the resilient membrane upon rotation of the drive element.

The resilient membrane may be a first resilient membrane and, a secondary resilient membrane may be disposed on the outside of the housing on a side of the first resilient membrane remote from the drive element, to define a closed intermediate pressure cavity between the first and second resilient membranes, such that when the first resilient membrane is deformed by the drive mechanism, a negative pressure is created in the intermediate pressure cavity which causes the second resilient membrane to deflect inward into the intermediate pressure cavity to generate a negative pressure in a vacuum chamber of a breast pump.

The housing may include an aperture and the resilient membrane may be disposed over the aperture.

The resilient membrane may be disposed on the outside of the housing and the flexible strap may extend from the drive element, through the aperture to the resilient membrane.

The flexible strap may be a discontinuous member having a first end which is connected to the drive element and a second, opposite end which is connected to the resilient membrane.

The motor may be coupled to a gearbox and the drive element may be coupled to an output shaft of the gearbox.

The drive mechanism may be configured such that the drive element rotates in a reciprocating movement back and forth to alternately pull and release the resilient membrane.

A second aspect of the present invention provides a breast pump comprising a drive mechanism as described above and, a vacuum chamber coupled to the housing, the vacuum chamber comprising a receptacle and a breast-receiving funnel in fluid communication with the receptacle, wherein when a woman's breast is placed in the breast-receiving funnel, the vacuum chamber is sealed closed such that deformation the resilient membrane creates a negative pressure in the vacuum chamber.

The vacuum chamber may include a drainage aperture having a one-way valve to allow expressed milk to exit the vacuum chamber but to prevent air entering the vacuum chamber through the drainage aperture.

The breast pump may comprise a fitting to enable a milk-collection bottle having a co-operating fitting to be coupled to the vacuum chamber over the drainage aperture.

The resilient membrane may extend into the vacuum chamber.

A third aspect of the present invention provides a method of generating a negative pressure in a vacuum chamber of a breast pump using a drive mechanism which comprises a housing, a motor coupled to a rotatable drive element within the housing, a resilient membrane coupled to the housing and, a flexible strap coupled between the drive element and the resilient membrane, the method comprising rotating the drive element to cause the flexible strap to pull and resiliently deform the resilient membrane to create the negative pressure in a vacuum chamber of a breast pump.

DETAILED DESCRIPTION OF EMBODIMENTS

Figure 1:
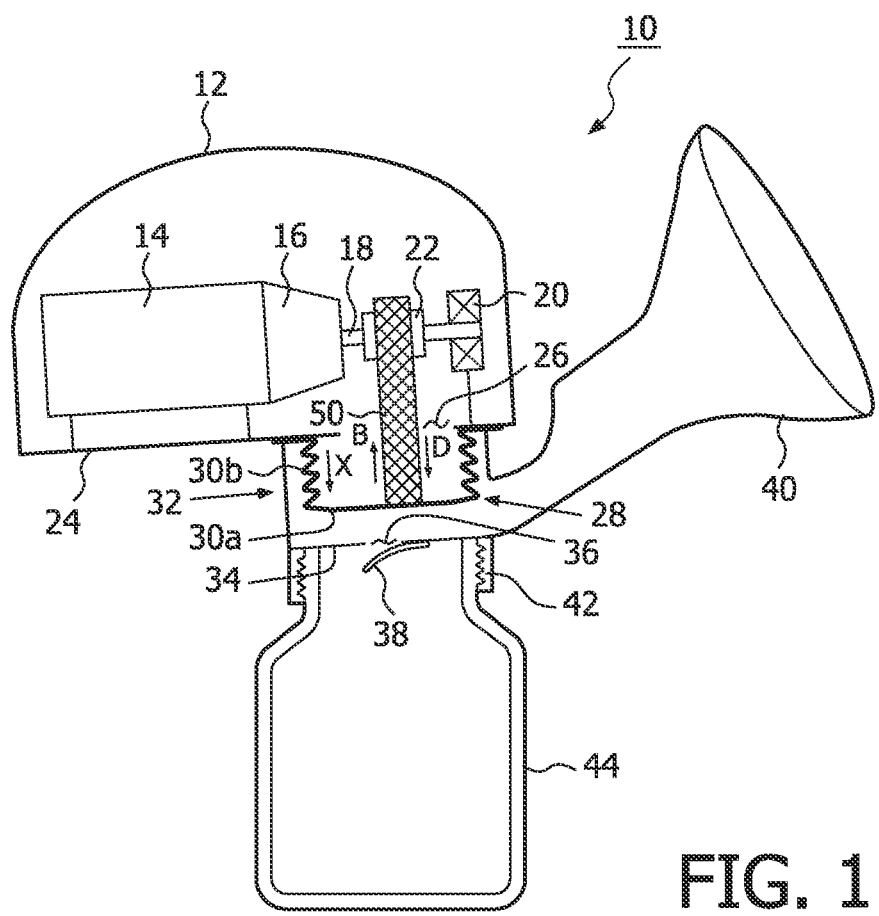
FIG. 1 shows a schematic cross-sectional view of a breast pump comprising a first aspect of the invention.
Figure 2:
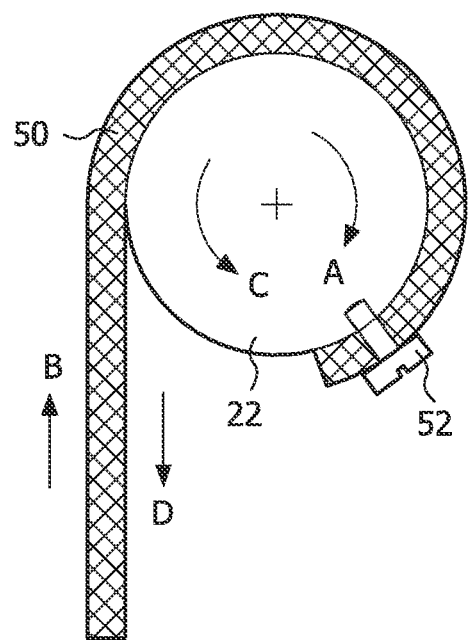
FIG. 2 shows a schematic end view of the drive wheel and flexible strap of the breast pump of FIG. 1.

Referring now to FIGS. 1 and 2, a breast pump 10 incorporating a drive mechanism of a first embodiment of the invention is shown and comprises a housing 12 containing a drive motor 14 coupled to a reduction gearbox 16. A drive shaft 18 extends from the gearbox 16 and is supported at its distal end in a support bearing 20. A drive wheel 22 is mounted on the drive shaft 18 between the gearbox 16 and the support bearing 20.

The housing 12 includes a base 24 on which the motor 14 and support bearing 20 are mounted, and the base 24 has an aperture 26 extending there through. The aperture 26 is sealed closed on the outside of the housing 12 by a resilient membrane 28 comprising a disc portion 30a and a bellows section 30b extending between a peripheral edge of the disc portion 30a and the base 24 of the housing 12 around the aperture 26.

A vacuum chamber 32 is coupled to the base 24 of the housing 12 over the aperture 26 and resilient membrane 28 so that the resilient membrane 28 extends into the vacuum chamber 32. The vacuum chamber 32 is of a generally cylindrical shape with one end of the cylindrical chamber being coupled to the housing 12 and sealed around the aperture 26 as described above, and the other end of the cylindrical chamber having a bottom wall 34. A breast-receiving funnel 40 extends from one side of the cylindrical side wall of the vacuum chamber 32 and is in fluid communication with the vacuum chamber 32. The bottom wall 34 includes a exit port 36 and a one-way valve 38 which covers the exit port 36 such that fluid may only pass from within the vacuum chamber 32 to the outside thereof, but the valve 38 prevents fluid from passing into the vacuum chamber 32 though the exit port 36. Thereby, when the valve 38 is closed and the funnel 40 is closed by a breast from which milk is to be expressed, the vacuum chamber 32 is a closed cavity.

The outside of the vacuum chamber 32 around the bottom wall 34 is provided with a screw thread 42 which is configured to be coupled with a milk-collection bottle 44 to receive expressed milk through the exit port 36 via the one-way valve 38.

The bellows section 30b of the resilient membrane 28 biases the disc portion 30a away from the housing 12 in the direction shown by arrow X in FIG. 1. A discontinuous strap 50 is coupled at one end to the drive wheel 22 and at the other end, to the centre of the disc portion 30a of the resilient membrane 28. As can be seen from the schematic drawing of FIG. 2, the strap 50 is coupled to the curved edge face of the drive wheel 22 and secured in place using a screw 52. Therefore, rotation of the drive wheel 22 in the direction of arrow A in FIG. 2 will cause the strap 50 to be wound around the drive wheel 22 and thereby will result in the strap 50 pulling upwardly on the resilient membrane 28 in the direction of arrow B as shown in FIGS. 1 and 2. Conversely, rotation of the drive wheel 22 in the direction of arrow C in FIG. 2 will cause the strap 50 to be unwound from around the drive wheel 22 and thereby will result in the strap 50 releasing any downward tension exerted by the resilient membrane 28, thereby allowing it to move under the biasing force of the bellows section 30b in the direction of arrow D as shown in FIGS. 1 and 2. It should be noted that the resilience of the disc portion 30a also contributes to the resistance force exerted on the flexible strap 50 away from the drive wheel 22, as well as the resistance of the bellows section 30b described above.

Operation of the apparatus of the first embodiment of the invention will now be described. Firstly, a milk-collection bottle 44 is coupled to the housing 12 by the screw thread 42 as shown in FIG. 1. The woman then places her breast in the breast-receiving funnel 40, thereby sealing closed the vacuum chamber 32. The breast pump is then switched on and the motor 14, via the gearbox 16, rotates the drive shaft 18 and thereby causes the drive wheel 22 to rotate. The rotating movement of the drive wheel is a reciprocating movement back and forth, alternating in clockwise and anti-clockwise directions.

Firstly, the drive wheel 22 rotates in the clockwise direction shown by arrow A in FIG. 2 and the strap 50 is wound around the drive wheel 22, thereby pulling upwards on the resilient membrane 28 as shown by arrow B in FIGS. 1 and 2. This causes the resilient membrane 28 to be deflected upwards in the direction of arrow B. As the one way valve 38 closes the exit port 36 and the open end of the breast-receiving funnel 40 is closed by the woman's breast, the vacuum chamber 32 is a closed cavity. Therefore, deflection of the resilient membrane 28 increases the volume of the closed vacuum chamber 32 and thereby creates a negative pressure within the vacuum chamber 32, which induces the woman's breast to express milk into the funnel 40, which then flows into the lower part of the vacuum chamber at the bottom wall 34 thereof.

The motor 14, via the gearbox 16, then rotates the drive shaft 18 in the opposite direction, shown by arrow C in FIG. 2, and thereby causes the drive wheel 22 to rotate that opposite direction.

As seen in FIG. 2, when the drive wheel rotates in the anti-clockwise direction shown by arrow C, the strap 50 is un-wound from around the drive wheel 22 by being pulled downwards by the biasing force of the resilient membrane 28, as shown by arrow D in FIGS. 1 and 2. This causes the resilient membrane 28 to return in the direction of arrow D to its original un-deflected state and so decreases the volume of the closed vacuum chamber 32 and thereby cancels the negative pressure within the vacuum chamber 32.

Once the negative pressure in the vacuum chamber 32 has been removed, the collected milk in the vacuum chamber 32 can pass through the one-way valve 38 and through the exit port 36 into the milk collection bottle 44.

The above process is then repeated with the motor 14 driving the drive wheel 22 to rotate in the clockwise direction again to create a negative pressure in the vacuum chamber 32 and then driving the drive wheel 22 in the opposite direction to cancel the negative pressure, and continues to be repeated until the woman has expressed the desired quantity of milk.

A second embodiment of a drive mechanism and breast pump of the invention will now be described with reference to FIGS. 3 and 4. As with the first embodiment of the invention described above, the breast pump 110 includes a housing 112 containing a drive motor 114 coupled to a reduction gearbox 116. A drive shaft 118 extends from the gearbox 116 and is supported at its distal end in a support bearing 120. A drive wheel 122 is mounted on the drive shaft 118 between the gearbox 116 and the support bearing 120.

Also as with the first embodiment, the housing 112 includes a base 124 on which the motor 114 and support bearing 120 are mounted, and the base 124 has an aperture 126 extending there through. However, the drive mechanism of the second embodiment of the invention differs from that of the first embodiment in that the aperture 126 is sealed closed on the inside of the housing 112 by a first resilient membrane 128 comprising a disc portion 130a and a bellows section 130b extending between a peripheral edge of the disc portion 130a and the inside of the base 124 of the housing 112 around the aperture 126.

The second embodiment of the invention further comprises a second resilient membrane 129 which is disposed on the outside of the base 124 of the housing 112 around the aperture 126. The second resilient membrane 129 is sealed around the aperture 126 such that a closed intermediate cavity is 133 is defined between the first and second resilient membranes 128,129.

A vacuum chamber 132 is coupled to the base 124 of the housing 112 over the aperture 126 and second resilient membrane 129 so that the second resilient membrane 129 extends into the vacuum chamber 132. The vacuum chamber 132 is of a generally cylindrical shape with one end of the cylindrical chamber being coupled to the housing 112 and sealed around the aperture 126 as described above, and the other end of the cylindrical chamber having a bottom wall 134. A breast-receiving funnel 140 extends from one side of the cylindrical side wall of the vacuum chamber 132 and is in fluid communication with the vacuum chamber 132. The bottom wall 134 includes an exit port 136 and a one-way valve 138 which covers the exit port 136 such that fluid may only pass from within the vacuum chamber 132 to the outside thereof, but the valve 138 prevents fluid from passing into the vacuum chamber 132 though the exit port 136. Thereby, when the valve 138 is closed and the funnel 140 is closed by a breast from which milk is to be expressed, the vacuum chamber 132 is a closed cavity.

The outside of the vacuum chamber 132 around the bottom wall 134 is provided with a screw thread 142 which is configured to be coupled with a milk-collection bottle 144 to receive expressed milk through the exit port 136 via the one-way valve 138.

Figure 3:
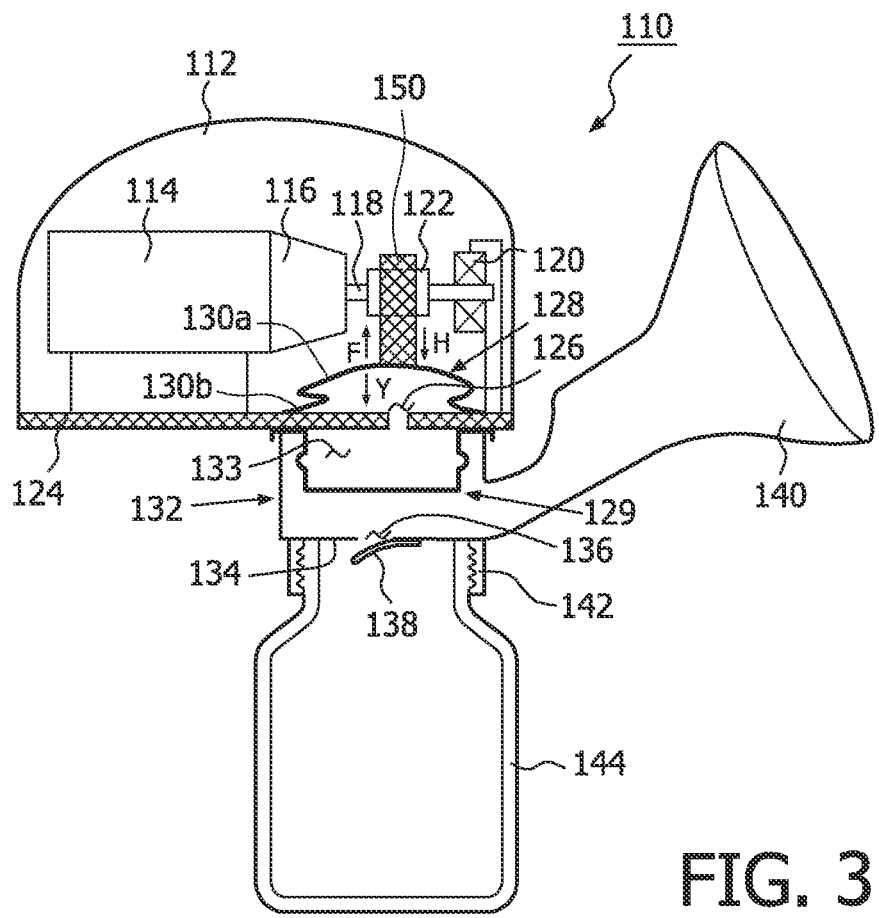
FIG. 3 shows a schematic cross-sectional view of a breast pump comprising a second aspect of the invention.

The bellows section 130b of the first resilient membrane 128 is configured such that it biases the disc portion 130a downwards towards the housing 112 and away from the drive wheel 122 in the direction shown by arrow Y in FIG. 3. A discontinuous strap 150 is coupled at one end to the drive wheel 122 and at the other end, to the centre of the disc portion 130a of the first resilient membrane 128. As can be seen from the schematic drawing of FIG. 4, the strap 150 and drive wheel 122 differ from the strap 50 and drive wheel 22 of the first embodiment of the invention described above, in that the drive wheel 122 includes a plurality of teeth 123 on its outer face, and the strap 150 includes a plurality of correspondingly shaped teeth 151 on one side thereof configured to engage and mesh with the teeth 123 of the drive wheel 122. The flexible strap 150 is coupled to the curved edge face of the drive wheel 122 and secured in place using a screw 152 such that the teeth 151 of the strap 150 are aligned with the gaps between the teeth 123 of the drive wheel 122 to enable the teeth 123,151 of each to mesh as the drive wheel is rotated.

Figure 4:
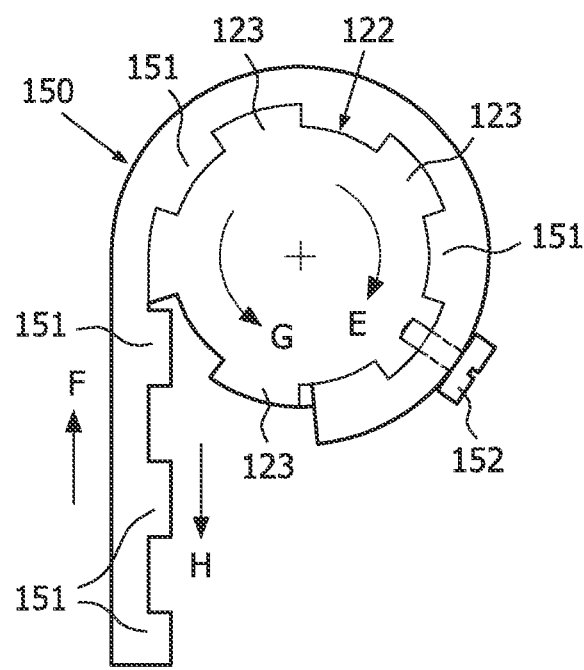
FIG. 4 shows a schematic end view of the drive wheel and flexible strap of the breast pump of FIG. 3.

Rotation of the drive wheel 122 in the direction of arrow E in FIG. 4 will cause the strap 150 to be wound around the drive wheel 122 with the respective teeth 123, 151 of the drive wheel 122 and strap 150 meshing, and thereby will result in the strap 150 pulling upwardly on the first resilient membrane 128 in the direction of arrow F as shown in FIGS. 3 and 4.

Conversely, rotation of the drive wheel 122 in the direction of arrow G in FIG. 4 will cause the strap 150 to be unwound from around the drive wheel 122 and thereby will result in the strap 150 releasing any downward tension exerted by the first resilient membrane 128, thereby allowing it to move under the biasing force of the bellows section 130b in the direction of arrow H as shown in FIGS. 3 and 4. It should be noted that the resilience of the disc portion 130a also contributes to the resistance force exerted on the flexible strap 150 away from the drive wheel 122, as well as the resistance of the bellows section 130b described above.

Operation of the apparatus of the second embodiment of the invention will now be described. Firstly, a milk-collection bottle 144 is coupled to the housing 112 by the screw thread 142 as shown in FIG. 3. The woman then places her breast in the breast-receiving funnel 140, thereby sealing closed the vacuum chamber 132. The breast pump is then switched on and the motor 114, via the gearbox 116, rotates the drive shaft 118 and thereby causes the drive wheel 122 to rotate. The rotating movement of the drive wheel 122 is a reciprocating movement back and forth, alternating in clockwise and anti-clockwise directions.

Firstly, the drive wheel 122 rotates in the clockwise direction shown by arrow E in FIG. 4 and the strap 150 is wound around the drive wheel 122, thereby pulling upwards on the first resilient membrane 128 as shown by arrow F in FIGS. 1 and 2. This causes the first resilient membrane 128 to be deflected upwards in the direction of arrow F. As the intermediate cavity 133 is a closed space, deflection of the first resilient membrane 128 increases the volume of the intermediate cavity 133 and thereby creates a negative pressure therein. Consequently, the negative pressure in the intermediate cavity 133 causes the second resilient membrane 129 to be deflected upwards into the intermediate cavity 133. Since the one way valve 138 closes the exit port 136 of the vacuum chamber 132 and the open end of the breast-receiving funnel 140 is closed by the woman's breast, the vacuum chamber 132 is also a closed cavity. Therefore, the upward deflection of the second resilient membrane 129 increases the volume of the vacuum chamber 132 and thereby creates a negative pressure therein, which induces the woman's breast to express milk into the funnel 140, which then flows into the lower part of the vacuum chamber 132 at the bottom wall 134 thereof.

The motor 114, via the gearbox 16, then rotates the drive shaft 118 in the opposite direction, shown by arrow G in FIG. 4, and thereby causes the drive wheel 122 to rotate that opposite direction.

As seen in FIG. 4, when the drive wheel 122 rotates in the anti-clockwise direction shown by arrow G, the flexible strap 150 is un-wound from around the drive wheel 122 by being pulled downwards by the biasing force of the first resilient membrane 128, as shown by arrow H in FIGS. 3 and 4. This causes the first resilient membrane 128 to return in the direction of arrow H to its original un-deflected state and so decreases the volume of the intermediate cavity 133, thereby cancelling the negative pressure therein. This has the effect of causing the second resilient membrane 129 to return in the direction of arrow H to its original un-deflected state and so decreasing the volume of the closed vacuum chamber 132, thereby cancelling the negative pressure within the vacuum chamber 132.

Once the negative pressure in the vacuum chamber 132 has been removed, the collected milk in the vacuum chamber 132 can pass through the one-way valve 138 and through the exit port 136 into the milk collection bottle 144.

The above process is then repeated with the motor 114 driving the drive wheel 122 to rotate in the clockwise direction again to create a negative pressure in the intermediate cavity 133 and thereby in the vacuum chamber 132, and then driving the drive wheel 122 in the opposite direction to cancel the negative pressure in the intermediate cavity 133 and thereby in the vacuum chamber 132, and the process continues to be repeated until the woman has expressed the desired quantity of milk The drive mechanisms described above may be configured to operate at a range of speeds, but it is found optimal that the rate of alternately creating and releasing negative pressure in the vacuum chamber is between 0.5-2 Hz.

In the above-described embodiments, it is stated that the motor alternately drives the drive wheel in the clockwise direction and then the anti-clockwise direction. However, it is intended within the scope of the invention that the motor may only positively drive the drive wheel in the direction which causes the flexible strap to be wound up around the drive wheel. Then, instead of the motor positively driving the drive wheel in the opposite direction, it may simply cease drive to the drive wheel and thereby allow the resilient force of the resilient membrane pulling on the flexible strap to unwind the flexible strap from around the drive wheel and allow the resilient membrane to return to its original un-deflected state, thereby causing the drive wheel to 'free-wheel' in the un-winding direction.

Both embodiments of the drive mechanism described above comprise a drive wheel mounted to the rotatable drive shaft, with the flexible strap secured to the drive wheel. However, it is intended within the scope of the invention that alternative drive elements may be included. For example, the drive wheel may be omitted entirely and the flexible strap may be attached directly to the drive shaft in order to be wound around the drive shaft and thereby pull on the resilient membrane. Alternatively, a protruding element such as an arm, may extend perpendicularly or otherwise, from the drive shaft, and the end of the flexible strap may be attached to the end of the protruding element remote from the drive shaft such that rotation of the drive shaft rotates the protruding element to thereby pull on the flexible strap by the leverage of the protruding element about the axis of the drive shaft.

Although the drive wheel 22 and flexible strap 50 of the first embodiment of the invention are described as having flat faces, whereas the drive wheel 122 and flexible strap 150 of the second embodiment of the invention are described as including inter-engaging teeth 129,151, it is intended within the scope of the invention that the drive wheel and flexible strap of the first embodiment of the invention may include such inter-engaging teeth, and conversely, the drive wheel and flexible strap of the second embodiment of the invention may have flat faces.

The resilient membranes 28,128 of the embodiments of the invention described above are defined as including corrugated bellows sections 30b,130b. However, it is intended within the scope of the invention that the resilient membranes may alternatively not include such bellows sections, and the deformation and biasing force against the pull of the flexible straps could be provided solely by the resilience of the membrane material.

The above-described embodiments comprise one drive wheel mounted on a drive shaft, with one flexible strap extending between the drive wheel and the resilient membrane. However, the scope of the invention is intended to cover alternative embodiments which may include a plurality of drive wheels or drive elements, and/or a plurality of flexible straps extending between the drive wheel(s)/element(s) and the resilient membrane.

The drive mechanism of the invention and a breast pump including such a drive mechanism provide numerous advantages over known breast pumps and breast pump drive mechanisms. For example, the pure rolling movement of the drive element and flexible strap means that there is no friction, unlike in, for example, rack and pinion type mechanisms. This means that the mechanism is more energy efficient and no lubrication is needed. It also means that the mechanism is virtually silent, as there is no play between the components and no 'stick-slip' of parts.

Further to the above, the drive mechanism of the invention allows high manufacturing tolerances, hence the lack of play between component parts of the mechanism. Also, the mechanism can be configured such that the flexible strap is pre-tensed—that is, in its most extended state before the drive element pulls on the flexible strap to deform the resilient membrane, the membrane could have an initial degree of deformation to keep the flexible strap taut and to ensure a silent movement without play.

Further advantages of the drive mechanism of the invention are the inherent robustness of the construction, the suitability for a compact design, and the low pump noise due to isolation of motor and gearbox vibration. Further, the linear relationship between the drive shaft rotation and the movement of the resilient membrane improves electronic programmability of the breast pump.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A drive mechanism for generating a negative pressure in a vacuum chamber of a breast pump, the drive mechanism comprising:
   a housing;
   a motor coupled to a rotatable drive element within the housing;
   a resilient membrane coupled to the housing; a flexible strap coupled between the drive element and the resilient membrane, wherein the flexible strap is a discontinuous member having a first end which is securely connected to the drive element and a second, opposite, end connected to the resilient membrane,
wherein rotation of the drive element causes the flexible strap to pull and resiliently deform the resilient membrane to create the negative pressure in a vacuum chamber of a breast pump.

2. The drive mechanism according to claim 1 wherein the drive element comprises a drive wheel.

3. The drive mechanism according to claim 2 wherein the drive wheel includes a plurality of teeth and the flexible strap includes a corresponding shaped plurality of teeth formed on one side thereof for engagement with the teeth on the drive wheel.

4. The drive mechanism according to claim 2 wherein the resilient membrane includes a bellows section which is deformed when the flexible strap pulls on the resilient membrane upon rotation of the drive element.

5. The drive mechanism according to claim 1 wherein said resilient membrane is a first resilient membrane and, a secondary resilient membrane is disposed on the outside of the housing on a side of the first resilient membrane remote from the drive element, to define a closed intermediate pressure cavity between the first and second resilient membranes, such that when the first resilient membrane is deformed, a negative pressure is created in the intermediate pressure cavity which causes the second resilient membrane to deflect inward into the intermediate pressure cavity to generate a negative pressure in a vacuum chamber of a breast pump.

6. The drive mechanism according to claim 1 wherein the housing includes an aperture and the resilient membrane is disposed over the aperture.

7. The drive mechanism according to claim 6 wherein the resilient membrane is disposed on the outside of the housing and the flexible strap extends from the drive element, through the aperture to the resilient membrane.

8. The drive mechanism according to claim 1 wherein the motor is coupled to a gearbox and the drive element is coupled to an output shaft of the gearbox.

9. The drive mechanism according to claim 1 configured such that the drive element rotates in a reciprocating movement back and forth to alternately pull and release the resilient membrane.

10. A breast pump comprising:
 a drive mechanism comprising:
  a housing;
  a motor coupled to a rotatable drive element within the housing;
  a resilient membrane coupled to the housing;
  a flexible strap coupled between the drive element and the resilient membrane, wherein the flexible strap is a discontinuous member having a first end which is securely connected to the drive element and a second, opposite, end connected to the resilient membrane, wherein rotation of the drive element causes the flexible strap to pull and resiliently deform the resilient membrane; and,
 a vacuum chamber coupled to the housing, the vacuum chamber comprising:
  a receptacle and a breast-receiving funnel in fluid communication with the receptacle, wherein when a woman's breast is placed in the breast-receiving funnel, the vacuum chamber is sealed closed such that deformation the resilient membrane creates a negative pressure in the vacuum chamber.

11. The breast pump according to claim 10 wherein the vacuum chamber includes a drainage aperture having a one-way valve to allow expressed milk to exit the vacuum chamber and to prevent air entering the vacuum chamber through the drainage aperture.

12. The breast pump according to claim 11 comprising a fitting to enable a milk-collection bottle having a co-operating fitting to be coupled to the vacuum chamber over the drainage aperture.

13. The breast pump according to claim 10 wherein the resilient membrane extends into the vacuum chamber.

* * * * *